United States Patent [19]

Waitz et al.

[11] 4,375,542
[45] Mar. 1, 1983

[54] KIJANIMICIN ANTIBIOTICS AND DERIVATIVES THEREOF

[75] Inventors: Jay A. Waitz, Far Hills; Mahesh G. Patel, Verona; Ann C. Horan, Metuchen, all of N.J.

[73] Assignee: Schering Corporation, Kenilworth, N.J.

[21] Appl. No.: 195,048

[22] Filed: Oct. 8, 1980

Related U.S. Application Data

[63] Continuation-in-part of Ser. No. 112,760, Jan. 17, 1980, abandoned.

[51] Int. Cl.³ .................. C07H 17/08; C12P 19/62
[52] U.S. Cl. .................................. 536/7.1; 424/180; 424/181; 435/76
[58] Field of Search ................................ 536/4, 17 R

[56] References Cited

U.S. PATENT DOCUMENTS

| | | | |
|---|---|---|---|
| 3,364,113 | 1/1968 | Friedmann et al. | 536/4 |
| 3,365,442 | 1/1968 | Ratsimamanga et al. | 536/4 |
| 3,723,410 | 3/1973 | Persinos | 536/4 |
| 4,082,858 | 4/1978 | Morita et al. | 536/4 |

*Primary Examiner*—Johnnie R. Brown
*Attorney, Agent, or Firm*—Gerald F. Swiss; Gerald S. Rosen; Bruce M. Eisen

[57] ABSTRACT

*Actinomadura Kijaniata* nov. sp produces a novel antibiotic which we have designated kijanimicin. The antibiotic or cationic salts thereof exhibit anti-acne, antitumor, antimalarial, antibacterial and anti-inflammatory activity.

7 Claims, No Drawings

KIJANIMICIN ANTIBIOTICS AND DERIVATIVES THEREOF

SUMMARY OF THE INVENTION

This application is a continuation-in-part of co-pending application Ser. No. 112,760, filed Jan. 17, 1980, now abandoned.

This invention relates to a novel microorganism and to the novel compositions of matter produced thereby. More particularly, this invention relates to the antibiotic kijanimicin and to the novel actinomycete of the genus Actinomadura herein designated *Actinomadura kijaniata* nov sp. which produces said antibiotic. The invention also relates the antibiotic's use as an antiacne agent, to its use as an antitumour agent, to its use as an antimalarial agent to its use as an antibacterial agent and to its use as an anti-inflammatory agent.

THE INVENTION

A novel actinomycete herein designated *Actinomadura kijaniata* nov sp. SCC 1256 upon being fermented under controlled aerobic conditions in a medium containing an assimilable source of carbon oxygen and nitrogen produces a novel antibiotic complex.

*Actinomadura kijaniata* nov sp. SCC 1256 was isolated from a soil sample collected in Kenya, Africa. A culture of this microorganism has been made a part of the permanent collection of the Northern Utilization and Research Division, Agricultural Research Service, U.S. Department of Agriculture, Peoria, Ill. where it has been assigned accession number NRRL 12069. A culture of the microorganism has also been made a part of the collection of the American Type Culture Collection (ATCC) Rockville, Md., where it has been assigned the accession number ATCC 31588.

THE MICROORGANISM

The strain, SCC 1256, has the following morphologic characteristics when grown on yeast-extract dextrose agar at 30° C. for 14–21 days. Abundant, curled aerial mycelia which fragment into long chains of eliptical spores approximately 1.0 to 1.5 microns in diameter by 15 to 2.0 microns in length are formed. The vegetative mycelia forms abundant branches.

The organism contains meso-diaminopimelic acid (meso-DAP) as a characteristic amino acid in the cell wall. Whole cells contain 3-O-methyl-D-galactose (madurose).

Table 1 reports the cultural characteristics of SCC 1256 cultivated on various standard media suggested by Shirling and Gottlieb (Inter. J. Syst. Bact. 16,313–340, 1966) and Waksman (The Actinomycetes, Vol II, The Williams and Wilkins Co., 1961). Observations were made after 14–21 days at 30° C. The color designations assigned to the vegetative mycelial pigments consisted of a color name (Descriptive Color Names Dictionary, Container Corp. America, 1950) and a color-chip number (Color Harmony Manual, ed. 4, Container Corp. America, 1958). The principal color of the vegetative mycelia is dark green, aerial mycelia in mass is white and is abundantly formed on ISP medium #7, starch agar and yeast-extract-dextrose agar.

The physiologic characteristics and carbohydrate utilization of strain 1256 are set forth in Tables 2 and 3 respectively.

Morphologic and cell wall analysis indicate that strain SCC 1256 is a species of the genus Actinomadura. None of the described species of Actinomadura (Cross & Goodfellow, Actinomycetales, Characteristics and Practical Importance, London, Academic Press, 1973; Nonomura, Jap. J. Ferment 52:71–77, 1974; Preobrazhenskaya and Sveshnikova, Microbiol 43:864–868, 1974) share the combination of dark green vegetative mycelia, white aerial mycelia and physiologic characters of SCC 1256. In addition, none produce the antibiotic kijanimicin. The culture is therefore considered a novel species of the genus Actinomadura designated *A. kijaniata* nov. sp. SCC 1256, NRRL 12069, ATCC 31588.

TABLE 1

Growth Characteristics of A. Kijaniata on Various Descriptive Media

| Medium | Growth Characteristics |
|---|---|
| Bennett's Agar | G: +++, good |
| | S: Raised, folded |
| | AM: Present, sparse, white |
| | DFP: Absent |
| | C: g 22 li, pine green |
| Czapek Sucrose Agar | G: +++, good |
| | S: Ribbon-like |
| | AM: Absent |
| | DFP: Absent |
| | C: g 22 n, dark pine green |
| Glucose-Asparagine Agar | G: +++, good |
| | S: Raised, folded |
| | AM: Present, sparse, white specs |
| | DFP: Absent |
| | C: g 22 n, dark pine green |
| Glycerol-Asparagine Agar | G: +++, good |
| | S: Flat, folded |
| | AM: Absent |
| | DFP: Gray, red brown |
| | C: Center, g 19 po, dark laurel periphery, g 6 ie, redwood |
| Nutrient Agar | G: +++, good |
| | S: Raised, folded |
| | AM: Absent |
| | DFP: Faint dull green |
| | C: g 23 n, evergreen |
| Water Agar | G: ±, poor |
| | S: Granular |
| | AM: Absent |
| | DFP: Absent |
| | C: g 24 ge, dusty green |
| Yeast-Extract Malt-Extract Agar (ISP No. 2) | G: +++, good |
| | S: Raised, hard, folded |
| | AM: Present, white specs |
| | DFP: Absent |
| | C: center, g 21 nl, dark jade green periphery, g 2 ec, biscuit |
| Potato-Dextrose Agar | G: ++, moderate |
| | S: Flat to slightly raised |
| | AM: Absent |
| | DFP: Absent |
| | C: g 2 ge, covert tan |
| Emerson's Agar | G: + to ++, fair to moderate |
| | S: Flat, granular |
| | AM: Absent |
| | DFP: Absent |
| | C: g 22 ig, bayberry |
| NZA Glucose Agar | G: +++, good |
| | S: Soft, compactly folded |
| | AM: Absent |
| | DFP: Absent to dark brown |
| | C: g 15 po, dark slate |
| Yeast-Extract Glucose Agar | G: +++, good |
| | S: Raised, deeply folded, hard cracking |
| | AM: Present, white |
| | DFP: Absent |
| | C: Center, g 22 ig, almond green periphery, g 3 ge, camel |
| Tomato-Paste Oatmeal Agar | G: +++, good |
| | S: Flat, granular |
| | AM: Present, white specs |

TABLE 1-continued
Growth Characteristics of A. Kijaniata on Various Descriptive Media

| Medium | Growth Characteristics |
|---|---|
| Starch Agar (Waksman No. 21) | DFP: Absent<br>C: g 1½ li, light olive darb<br>G: +, fair<br>S: Flat, granular<br>AM: Absent |
| Calcium-Maleate Agar (Waksman No. 7) | DFP: Absent<br>C: g 24 ig, sage green<br>G: + to ++, fair to moderate<br>S: Plicate, soft<br>AM: Absent |
| Oatmeal Agar (ISP No. 3) | DFP: Absent<br>C: g 2 gc, bamboo<br>G: + to ++, fair to moderate<br>S: Flat, granular<br>AM: Present, white specs |
| Inorganic Salts - Starch Agar (ISP No. 4) | DFP: Absent<br>C: g 22 nl, dark pine green<br>G: +, fair<br>S: Flat, granular<br>AM: Absent |
| Peptone-Iron Agar | DFP: Faint green<br>C: Center, g 23 li, slate green periphery, g 4 ge, light fawn<br>G: ++, moderate<br>S: Raised, granular<br>AM: Present, white specs |
| Casein Agar | DFP: Absent<br>C: g 2 ge, covert tan<br>G: ++, moderate<br>S: Flat, granular<br>AM: Absent |
| Tyrosine Agar (ISP No. 7) | DFP: Absent<br>C: g 22 ih, moss gray<br>G: +++, good<br>S: Raised, folded<br>AM: Present, abundant, white |
| Starch Agar (Yeast) | DFP: Absent<br>C: g 5 ih, lead gray<br>G: +++, good<br>S: Hard, folded<br>AM: Present, moderate, white |
| Calcium Citrate Agar | DFP: Absent<br>C: g 23 li, slate green<br>G: +, fair<br>S: Flat, granular<br>AM: Absent |
| Gelatin Agar (McDade) | DFP: Absent<br>C: g 2 li, covert brown<br>G: ++, moderate<br>S: Raised, compactly folded<br>AM: Absent |
| | DFP: Absent<br>C: Center, g 1 po, ebony periphery, g 1 fe, greige |

G, growth;
S, surface characteristics;
AM, aerial mycelium;
DFP, diffusable pigments; and
C, color of the growth.

TABLE 2
Physiologic Properties of A. Kijaniata

| TEST | A. KIJANIATA Results |
|---|---|
| Hydrolosis of: | |
| Adenine | + |
| Hypoxanthine | + |
| Tyrosine | + |
| Xanthine | + |
| Casein | + |
| Starch | +, Weakly Positive |
| Gelatin | + |
| Nitrate to Nitrite | Weakly Positive |
| Growth in the presence of NaCl | |
| 1.0% | +++, good |
| 2.0% | ++, moderate |
| 3.0% | +, fair to poor |
| Growth at | |
| 28° C. | +++, good |
| 35° C. | +++, good |
| 40° C. | ++, fair to moderate |
| 45° C. | +, fair |
| Formation of | |
| H$_2$S | Negative |
| Melanin | Negative |

TABLE 3
Utilization of Carbohydrates

| TEST Carbohydrates[1] | A. KIJANIATA |
|---|---|
| Control | − |
| D-Arabinose | + |
| L-Arabinose | + |
| Dextrin | + |
| Dulcitol | − |
| Erythritol | − |
| D-Fructose | + |
| L-Fucose | + |
| D-Galactose | + |
| D-Glucose | + |
| α-m-d-glucoside | − |
| m-β-D-glucopyranoside | + (green dfp) |
| Glycerol | + |
| Inositol | + |
| Inulin | − |
| Lactose | − |
| Maltose | + |
| D-Mannitol | − |
| D-Mannose | + |
| Melibiose | − |
| Melizitose | − |
| Raffinose | − |
| L-Rhamnose | + |
| Ribose | + |
| Sucrose | + |
| Trehalose | + |
| D-Xylose | + |

[1]Medium of Luedemann and Brodsky Antimicrobial Agents and Chemotherapy, 1963, pg. 116–124 (1964)

THE FERMENTATION

*A. kijaniata* when fermented under controlled conditions in a suitable medium, produces an antibiotic herein designated kijanimicin.

The fermentation which produces the antibiotics is commenced by the production of a vigorous vegetative inoculum which is usually produced in two or three stages. A suitable medium for preparing such inoculum is set forth herein below as Medium A and Medium B. The inoculum and the fermentation conducted in a medium wherein the pH is maintained at from about 6.5 to about 8.5, preferably about 7.5 for the inoculum and 7.0 for the fermentation. The proper pH ranges are usually maintained by the incorporation of suitable buffers, such as calcium carbonate in the media.

The vegetative inoculum and the fermentation are effected at from about 25° C. to about 45° C., preferably between 28° C. and 35° C. The most preferred temperature in which to prepare the vegetative inoculum and to conduct the fermentation is about 30° C.

In general, the nutrient media are prepared in a suitable fermentation vessel or flask, which is sterilized and cooled prior to inoculation. However, the media may be stored under aseptic conditions at sub-zero temperatures prior to use.

INOCULUM PREPARATION

In order to produce the antibiotic of this invention, a vigorously growing vegetative inoculum is preferred.

In general, inoculum preparation is carried out in two or more stages. For large scale fermentations (e.g. about 50 liters), it is preferred that the inoculum be prepared in three stages.

A suitable medium for preparing vegetative inocula are as follows:

| Medium A | |
| --- | --- |
| Beef Extract | 3 g |
| Tryptose | 5 g |
| Dextrose | 1 g |
| Potato Starch | 24 g |
| Yeast Extract | 5 g |
| Calcium Carbonate | 2 g |
| Tap Water to | 1.0 liter |

Two ml of freshly thawed whole broth of *A. kijaniata* is used to inoculate 50 ml of sterile medium A.

A. The flask is incubated at about 30° C. for from about 48 to about 96, preferably about 72 hours on a shaker at about 300 rpm and having a 2 inch throw.

SECOND INOCULUM STAGE

Twenty-five ml of the first inoculum is used to inoculate a series of 500 ml portions of sterile Medium A in two liter Erlenmeyer flasks. The flasks are incubated at about 30° C. for from about 24 to about 72, preferably 48 hours.

THIRD INOCULUM STAGE

Twenty-five ml of the second inoculum is used to inoculate each of a series of 500 ml portions or sterile Medium B in two liter Erlenmeyer flasks. The flasks are incubated with agitation at about 350 rpm and at about 30° C. for from about 24 to about 72, preferably 48 hours. Aeration at about 0.35 Volume of air/Volume of fermentation/minute (VVM).

The following medium has been found to provide both satisfactory and reproducible yields of antibiotic production.

| Medium B | |
| --- | --- |
| Yeast Extract | 5 g/liter |
| Dextrose | 10 g/liter |
| Soluble Starch | 20 g/liter |
| NZ Amine (Difco) | 5 g/liter |
| Calcium Carbonate | 4 g/liter |
| Cobalt Chloride | $10^{-6}$ M |
| Post-sterilization | pH 7.0 |

ANTIBIOTIC PRODUCTION

Ten liters of sterile Medium B is inoculated with 500 ml of second stage inoculum prepared as described above. Incubate the fermentation mixture at from about 27° C. to about 35° C., preferably about 30° C. with agitation and aeration at about 350 rpm and at 0.35 vvm, respectively. Maintain the pH of the fermentation at from about 6.8 to about 7.5 by the addition of dilute acid or alkali if necessary. The addition of dilute acid or dilute alkali is usually unnecessary. However, in a normal fermentation, the pH will climb to about 7.5 and will drop back to neutrality by the end of the fermentation.

ISOLATION AND PURIFICATION

Kijanimicin may be isolated by extraction using about two volumes of immiscible organic solvent e.g., (ethyl acetate) per extract and by extracting the broth twice. The extracts are combined, evaporated to a residue and dissolved in acetone. The product is precipitated by the addition of ether:hexane (6:4 v/v) solution. The resulting buff colored precipitate is filtered and dried in vacuo at about 40° C., to yield Kijanimicin.

Kijanimicin may be purified by chromatography on silica gel using a suitable solvent system.

Kijanimicin has a unique chemical structure. It contains a novel tetrasaccharide unit consisting of three molecules of L-digitoxose and one molecule of 4-O-methyl-L-digitoxose. The tetrasaccharide unit is attached to a secondary hydroxyl group in the aglycone. The antibiotic also has a novel branched chain nitrosugar, D-kijanose, which is also attached to a secondary hydroxyl group on the aglycone.

Kijanimicin is a colorless amorphous solid which decomposes at 174.5° C. and has the following characteristic physicochemical properties:

TABLE 3

Elemental Analysis
Found C, 60.78; H, 7.94; N, 1.96%.
$C_{67}H_{100}N_2O_{24}$[1] requires: C, 61.08; H, 7.65; N, 2.13; O, 29.14%.
pka 5.0
$\{\alpha\}_D^{26} -116.4°$ (C 0.3%, $CH_3OH$)
Ultraviolet Spectrum
$\lambda$max ($CF_3CH_2OH$) 199 nm ($E^{1\%}_{1\ cm}$ 328.4),
242 nm ($E_{1\ cm}^{1\%}$ 56.2), 264 nm ($E_{1\ cm}^{1\%}$ 63.1), 274 nm ($E_{1\ cm}^{1\%}$ 60.7).
$\lambda$max ($CH_3OH$/0.1N HCL) 260 nm ($E_{1\ cm}^{1\%}$ 60.8)
$\lambda$max ($CH_3OH$/0.1NaOH) 236 nm ($E_{1\ cm}^{1\%}$ 103.9), 265 nm ($E_{1\ cm}^{1\%}$ 86.1), 276 nm ($E_{1\ cm}^{1\%}$ 83.4).
Circular Dichroism
$\{\theta\}_{194} -176,016$, $\{\theta\}_{216} -176,016$, $\{\theta\}_{300} +11,479$ ($CF_3CH_2OH$),
Infrared Spectrum
$\lambda$max ($CHCL_3$) 3690, 3620, 3540, 3480, 3440, 2970, 2940, 1755, 1733, 1623, 1545, 1515, 1318, 1232, 1130, 1060 cm$^{-1}$.
$1_H$ Nuclear Magnetic Resonance
$\delta_H$ ($CDCl_3$) 0.65 (2H,m), 1.07 (3H,d,J=7 $H_z$) 1.18 (3H,d,J=6 $H_z$), 1.20-1.40 (envelope of signals), 1.60 (3H,s), 1.64 (3H,s), 3.45 (3H,s), 3.76 ppm. (3H,s)
$13_{C-NMR}$ Nuclear Magnetic Resonance
$\delta_C$ ($CDCl_3$) 206.2, 201.5, 167.1, 157.4, 141.5, 137.1, 135.7, 126.7, 125.8, 123.6, 121.5, 119.3, 101.9, 99.8, 98.2, 97.1, 92.2, 91.0, 90.8, 84.5, 83.3, 82.6, 79.6, 78.4, 72.4, 71.8, 69.1, 68.1, 67.5, 67.1, 66.8, 65.1, 65.9, 64.4, 63.8, 62.6, 57.3, 53.8, 53.2, 52.7, 51.0, 43.1, 41.6, 40.2, 38.5, 36.8, 35.7, 35.5, 34.8, 34.4, 31.3, 31.1, 29.9, 29.7, 27.9, 25.3, 22.2, 20.2, 18.4, 17.9, 17.9, 17.9, 17.0, 15.1, 15.1, 14.0, 13.7.

1. Determined by Plasma Desorption mass Spectrometry (Cf) on Kijanimicin methyl ether (1331.5±0.2, $C_{68}H_{102}N_2O_{24}$).

STABILITY

Kijanimicin is substantially stable at pH 6–10 at room temperature and up to 100° C. for at least 30 minutes. It loses activity rapidly at room temperature at pH 2–3.

STRUCTURE

On the basis of the foregoing physical data and x-ray crystallographic studies on the diacetyl of the aglycone, it has been determined that Kijanimicin has the following structural formula:

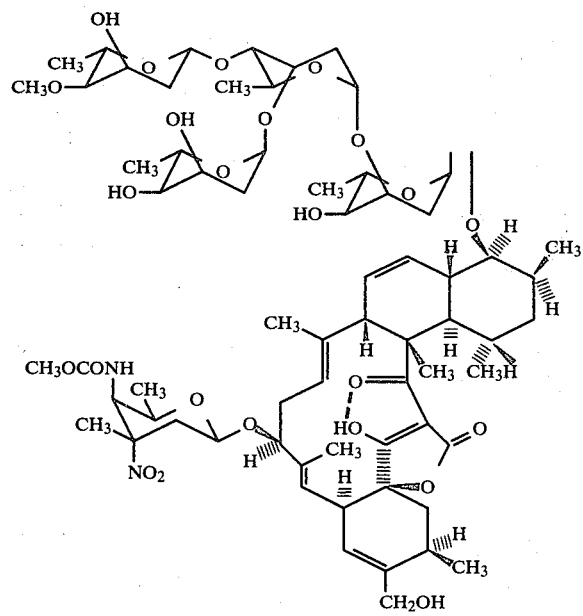

EXAMPLE 1

Isolation of Kijanimicin

Chromatograph 30.1 g of crude kijanimicin on a 4 kg silica gel column using 3.5% methanol in methylene chloride as the eluant. Collect 10 ml fractions while monitoring the column by thin layer chromatography on silica gel plates using 10% methanol in chloroform as the eluant. Combine fractions having the same mobility on the TLC Plates and evaporate to dryness to yield 9.3 g of kijanimicin. By combining slower moving fractions and evaporating them to dryness 5.5 g of kijanimicin may be obtained.

EXAMPLE 2

Sodium Salt of Kijanimicin

Add 7.6 g of kijanimicin to a stirred solution of 58.12 ml of 0.1 N sodium hydroxide in 800 ml of distilled water and continue stirring at 25° C. for five hours. Filter the solution through a fine glass sintered funnel and lyophilize the filtrate to yield 6.3 g of the sodium salt of kijanimicin as a colorless amorphous solid.

Found: C, 58.65; H, 7.49; N, 1.93; Na, 2.24%. $C_{67}H_{99}N_2O_{24}Na$ requires: C, 60.08; H, 7.45; N, 2.09; Na, 1.72% $[\alpha]_D^{26c} = -165.5°$ (0.3%, $H_2O$)

Ultraviolet λmax ($CF_3CH_2OH$) 197 nm ($E_{1\ cm}^{1\%}$ 304.5), 236 nm

Absorption ($E_{1\ cm}^{1\%}$ 65.2), 266 nm ($E_{1\ cm}^{1\%}$ 62.8), 272 nm ($E_{1\ cm}^{1\%}$ 62.8)

Infrared Absorption λmax (K Br) 3450, 2970, 2925, 1720, 1625, 1542, 1510, 1405, 1050 $cm^{-1}$.

In a similar manner, by using an equivalent quantity of other salt forming elements such as potassium, rubidium, and the like and by following substantially the process of this example, the corresponding kijanimicin salts may be prepared.

In like manner, by using an equivalent quantity of organic cation forming substrates such as N-methylglucamine or diethylamine and the like and by following substantially the process of this example, the corresponding kijanimicin salts may be prepared.

BIOLOGICAL ACTIVITY OF KIJANIMICIN

Acne is a condition for which the pathogenesis is not entirely known. However, it is known that the administration of certain antibiotics (e.g. tetracycline) have a beneficial therapeutic effect. The antibiotics exhibiting the greatest effect are those that are active against *Propionibacterium acnes*. This suggests that *P. acnes* plays a prominent role in the evolution of the disease. Apart from being active against *P. acnes*, an effective anti-acne agent should have a narrow spectrum of antimicrobial activity to lessen the potential for the development of resistant microorganisms. The agent should exhibit sufficient lipid solubility to penetrate the sebaceous gland, should have limited potential for irritation and sensitization and should possess antilipase properties thereby preventing the formation of inflammatory free fatty acids from sebum.

Kijanimicin satisfies the foregoing requirements. When tested against a multiplicity of strains of *P. acnes*, kijanimicin exhibited MIC's ranging from 0.37 to 1.5 mcg. per ml after 48 hours in Fluid Throglycolate Broth. The methodology used in vivo anti-acne testing is substantially the same as that set forth in U.S. Pat. No. 4,044,140, issued Aug. 23, 1977.

Kijanimicin is also active against strains of anaerobic bacteria other than *P. acnes*. For example, when tested in vitro, the antibiotic was active against strains of Peptococcus species, Peptostreptococcus and *E. lentum*.

Kijanimicin exhibits anti-tumor activity against P-388 leukemia when tested in vivo in mice to which a lethal dose has previously been administered.

Anti-tumor activity was determined by the standard National Cancer Institute test which was published in *Cancer Chemothr. Rep.* 3:1–103 1972.

In the test $10^6$ cells per mouse of P-388 leukemia (bleomycin sensitive) is administered intraperitoneally on day 1. The test compound is serially diluted (1/10, 1/100, etc.) and each dilution is administered to a mouse from day 1 to day 9. Animals dying on or before day 5 are listed as toxic deaths. Controls are run using bleomycin and olivomycin A. The results are calculated by the formula in which MST=medium survival time in days;

T=treated,
C=control
MST $T/C = MST-T/MST-Control \times 100$.

If $T/C \geq 125$ the test compound exhibits significant anti-tumor activity.

Kijanimicin also exhibits antiparasitic activity and is especially useful against strains of the malarial parasite, *Plasmodium berghei*. The activity was exhibited in experiments using $CF_1$, mice which were administered a lethal dose of the blood from previously infected mice, antibiotic therapy being commenced one day after infection.

Kijanimicin exhibits an anti-inflammatory effect when subjected to art recognized test procedures, such activity being especially advantageous in the treatment of acne.

Kijanimicin exhibits an oral $PD_{50}$ in mg/kg in mice against representative gram negative and gram positive bacteria ranging from 50 to over 100 as the sodium salt and from 10 to over 100 as the free antibiotic. The antibiotic exhibits a subcutaneous $PD_{50}$ in mg/kg against the same bacteria of from 10 to over 100 both as the sodium salt and as the free antibiotic.

Kijanimicin exhibits an oral and a subcutaneous $LD_{50}$ of greater than 1000 mg/kg. Thus, the oral and the subcutaneous $LD_{50}$ is about ten times the $PD_{50}$ (i.e. the therapeutic index is about 10).

In view of the foregoing, it can be seen that kijanimicin is chemically unique and biologically useful.

PHARMACEUTICAL FORMULATIONS

| CREAM | mg/g |
|---|---|
| Kijanimicin | 1.0 |
| Cetyl Alcohol | 40.0 |
| Stearyl alcohol | 40.0 |
| Isopropyl myristate | 100.0 |
| Polyoxyethylene (2) monostearyl ether[1] | 10.0 |
| Polyoxyethylene (20) monostearyl ether[1] | 25.0 |
| Propylene glycol | 100.0 |
| Benzyl alcohol | 10.0 |
| Purified water q.s. ad | 1.0 |

METHOD OF MANUFACTURE

Melt together and heat to about 70° C. the cetyl alcohol, stearyl alcohol, polyoxyethylene (2) monostearyl ether, polyoxyethylene ethylene (20) monostearyl ether and isopropyl myristate. Add the propylene glycol to water in a separate container, heat to 70° C. and dissolve in this aqueous phase the benzyl alcohol. Dissolve the kijanimicin in the aqueous phase while stirring. Add the aqueous phase to the oily phase with stirring. Cool the mixture with stirring until the temperature reaches 25° C., then transfer into suitable containers.

| CREAM | mg/g |
|---|---|
| Kijanimicin | 20.0 |
| Cetyl alcohol | 40.0 |
| Stearyl alcohol | 40.0 |
| Isopropyl myristate | 100.0 |
| Polyoxyethylene (2) monostearyl ether[1] | 10.0 |
| Polyoxyethylene (20) monostearyl ether[1] | 25.0 |
| Propylene glycol | 100.0 |
| Benzyl alcohol | 10.0 |
| Purified water q.s. ad | 1.0 g |

METHOD OF MANUFACTURE

Same as set forth above.
(1) ICI Americas, Inc. Wilmington, Del.

| GEL | mg/g | |
|---|---|---|
| Kijanimicin | 1.0 | 20.0 |
| Propylene glycol | 50.0 | 50.0 |
| Hydroxypropyl cellulose | 25.0 | 25.0 |
| Ethyl alcohol q.S. ad | 1.0 g | 1.0 g |

METHOD OF MANUFACTURE

Disperse the Kijanimicin in alcohol with agitation. Add the propylene glycol and then the hydroxypropylcellulose, maintaining agitation until the hydroxypropylcellulose is evenly dispersed.

| LOTION | | |
|---|---|---|
| Kijanimicin | 1.0 | 20.0 |
| Ethyl Alcohol | 450.0 | 450.0 |
| Polyethylene glycol 400 | 350.0 | 350.0 |
| Hydroxypropylcellulose | 5.0 | 5.0 |
| Propylene glycol q.S. ad | 1.0 | 1.0 |

METHOD OF MANUFACTURE

Dissolve or disperse kijanimicin in the solvent mixture of ethyl alcohol, polyethylene glycol 400 and propylene glycol with agitation. Then add the hydroxypropylcellulose maintaining agitation, until the hydroxypropylcellulose is evenly dispersed.

PARENTERALS

| (1) Injectable Solution | mg/ml |
|---|---|
| Kijanimicin | 10.00 |
| Methylparaben | 1.30 |
| Propylparaben | 0.20 |
| Sodium bisulfite | 3.20 |
| Disodium edetate | 0.10 |
| Sodium sulfate | 2.60 |
| Water for injection q.s. ad | 1.0 ml |

METHOD OF MANUFACTURE

1. Dissolve parabens in a portion (approx. 85% of the final volume) of the water for injection at 65°–70° C.
2. Cool to 25°–35° C. Charge and dissolve sodium bisulfite, disodium edetate and sodium sulfate.
3. Charge and dissolve the kijanimicin.
4. Bring the solution to the final volume by adding water for injection.
5. Filter the solution thru 0.22 micron membrane and fill into appropriate containers.
6. Terminally sterilize the units by autoclaving.

| (2) Injectable Suspension | mg/ml |
|---|---|
| Kijanimicin | 20.00 |
| Benzyl alcohol | 9.0 |
| Methylparaben | 1.8 |
| Propylparaben | 0.2 |
| Sodium carboxymethylcellulose | 5.0 |
| Polyethylene glycol 4000 | 10.0 |
| Povidone | 5.0 |
| Sodium citrate | 15.0 |
| Disodium edetate | 0.1 |
| Water for injection | q.s. 1.0 ml |

METHOD OF MANUFACTURE

1. Dissolve parabens in a portion of water for injection at 65°–70° C.
2. Cool to 25°–35° C. Charge and dissolve benzyl alcohol, sodium citrate, disodium edetate, PEG 4000, povidone and sodium carboxymethylcellulose.
3. Filter the solution and sterilize by autoclaving.
4. Make a slurry of kijanimicin and pass it through a colloid mill.
5. Mix it well with solution from Step 3 and pass it through the mill.
6. Bring the suspension to the final volume/weight and fill into sterile containers.

| ORAL CAPSULES INGREDIENT | mg/capsules | |
| --- | --- | --- |
| Kijanimicin Sodium Salt | 25.0 | 100.0 |
| Lactose, impalpable powder USP | 139.0 | 182.0 |
| Corn starch UPS | 30.0 | 105.0 |
| Magnesium stearate USP | 1.0 | 3.0 |
| Sodium lauryl sulfate | 5.0 | 10.0 |
| | 200.0 | 400.0 |

METHOD OF MANUFACTURE

Mix the kijanimicin sodium salt, lactose, cornstarch and Sodium Lauryl Sulfate in a suitable blender for 5 to 15 minutes. Pass through a fine screen (#40) if necessary. Reblend for 5 to 10 minutes; add the magnesium stearate and mix further for 3 to 5 minutes. Using a suitable machine, encapsulate the mixture into a two piece hard gelatin capsule of appropriate size.

We claim:

1. Kijanimicin, having the following physicochemical characteristics:
   (a) A melting point with decomposition of 174.5° C.;
   (b) A specific optical rotation as measured at the D line of sodium of 25° C. of $-116.4° \pm$ at 0.3% in methanol;
   (c) Ultra-violet absorption maxima in 2,2,2-trifluoroethanol at 99 nm ($E_{1\,cm}^{1\%}$ 328.4), 242 nm ($E_{1\,cm}^{1\%}$ 56.2), 264 nm ($E_{1\,cm}^{1\%}$ 63.1) and 274 nm ($E_{1\,cm}^{1\%}$ 60.7);
   (d) Infrared Spectrum, lambda max ($CHCL_3$) 3690, 3620, 3540, 3480, 3440, 2970, 2940, 1755, 1733, 1623, 1545, 1515, 1318, 1232, 1130, 1060 $cm^{-1}$;
   (e) $^{13}C$-NMR Nuclear Magnetic Resonance $\delta C$ ($CDCL_3$) 206.2, 201.5, 167.1, 157.4, 141.5, 137.1, 135.7, 126.7, 125.8, 123.6, 121.5, 119.3, 101.9, 99.8, 98.2, 97.1, 92.2, 91.0, 90.8, 84.5, 83.3, 82.6, 79.6, 78.4, 72.4, 71.8, 69.1, 68.1, 67.5, 67.1, 66.8, 65.1, 64.9, 64.4, 63.8, 62.6, 57.3, 53.8, 53.2, 52.7, 51.0, 43.1, 41.6, 40.2, 38.5, 36.8, 35.7, 35.5, 34.8, 34.4, 31.3, 31.1, 29.9, 29.7, 27.9, 25.3, 22.2, 18.4, 17.9,
   (f) $^1H$ Nuclear Magnetic Resonance $\delta H$ ($CDCl_3$)0.65 (2H,m), 1.06 (3H,d,J=7 $H_z$), 1.18 (3H,d,J-6$H_z$), 1.20-1.40 (envelop of signals), 1.60 (3H,S), 1.64 (3H,S), 3.45 (3H,S), 3.76 ppm (3H,S);
   (g) and having a planar structural formula substantially as follows:

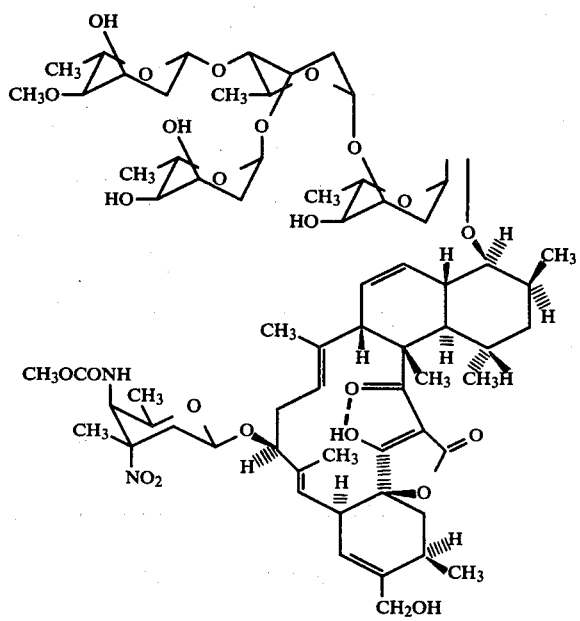

and the non-toxic pharmaceutically acceptable cationic salts thereof.

2. A compound of claim 1, said compound being kijanimicin.

3. A non-toxic pharmaceutically acceptable cationic salt of kijanimicin as defined in claim 1.

4. A salt of kijanimicin as defined in claim 5 selected from the group consisting of sodium, potassium, rubidium, N-methylglucamine and diethylamine.

5. A compound of claim 4, said compound being the sodium salt of kijanimicin.

6. A compound of claim 4, said compound being the N-methyl glucamine sale of kijanimicin.

7. A compound of claim 4, said compound being the diethylamine salt of kijanimicin.

* * * * *